United States Patent [19]
Igaki et al.

[11] Patent Number: 5,843,096
[45] Date of Patent: Dec. 1, 1998

[54] MEDICAL SUTURING MATERIAL

[76] Inventors: Keiji Igaki, 1-21, Wakakusa 2-chome, Kusatsu-shi, Shiga 525; Masatoshi Mori, Turn-dole Nishino II 203, 54 Nishinokishinoshita-Machi, Yamashina-ku, Kyoto-shi, Kyoto-fu 607; Shigeo Ohoi, 15-3, Amemiya, Mikata-cho, Ayabe-shi, Kyoto-fu 623, all of Japan

[21] Appl. No.: 765,882

[22] PCT Filed: May 8, 1996

[86] PCT No.: PCT/JP96/01219

§ 371 Date: Apr. 30, 1997

§ 102(e) Date: Apr. 30, 1997

[87] PCT Pub. No.: WO96/35376

PCT Pub. Date: Nov. 14, 1996

[30] Foreign Application Priority Data

May 8, 1995 [JP] Japan ................................. 7-109834
May 16, 1995 [JP] Japan ................................. 7-117541

[51] Int. Cl.[6] ................................................ H61B 17/08
[52] U.S. Cl. ........................... 606/151; 606/139; 606/215
[58] Field of Search ................................. 606/151, 139, 606/213, 215, 219, 220, 142, 143; 227/175.1, 182, 19, 901; 139/387 R, 389

[56] References Cited

U.S. PATENT DOCUMENTS

| 2,712,843 | 7/1955 | Ottinger et al. | 139/389 |
| 4,834,090 | 5/1989 | Moore | 128/303 |
| 5,312,132 | 5/1994 | Pillet | 280/743 R |
| 5,397,324 | 3/1995 | Carroll et al. | 606/139 |

FOREIGN PATENT DOCUMENTS

| 0577373 | 3/1994 | European Pat. Off. . |
| 0667119 | 8/1995 | European Pat. Off. . |
| 7-33342 | 6/1995 | Japan . |
| 8-47526 | 2/1996 | Japan . |

*Primary Examiner*—Michael Powell Buiz
*Assistant Examiner*—Tina T. D. Pham
*Attorney, Agent, or Firm*—Limbach & Limbach L.L.P.

[57] ABSTRACT

A medical suturing material which is loaded into an automatic suturing device having a staple line when used. The medical suturing material according to the present invention is formed into a bag shape having a closed leading end by sewing a sheet shape suturing material by using a suturing thread. The main material of the suturing material is unwoven fabric such as felt, woven fabric or a knit cloth having somewhat flexibility and stretchability. In particular, bioabsorbable polymer, such as polyglycolic acid or a portion of a tissue of an organism is employed. Since the suturing material according to the present invention is formed into the bag shape having a closed leading end by sewing, displacement taking place attributable to shrinkage in the insertion direction can be prevented when the automatic suturing device is inserted.

10 Claims, 4 Drawing Sheets

MEDICAL SUTURING MATERIAL

TECHNICAL FIELD

The present invention relates to a medical suturing material which is sutured to, for example, an excised portion of a tissue of an organism, and more particularly, to a medical suturing material of a type arranged to be loaded into an automatic suturing device.

BACKGROUND ART

Excision of a diseased part of a tissue of an organism generally is performed by a surgical operation. In order to reduce burden of a patient, the operation has been performed with an endoscope.

For example, an excision operation using an automatic suturing device has been performed. The automatic suturing device is introduced into the organism through a perforation to excise the diseased part and suture the excised portion. By using the medical suturing material, an advantage can be realized in that the necessity of incision of the diseased part can be eliminated. Therefore, the automatic suturing device has, at the leading end thereof, a suturing mechanism portion for holding the excised portion of the tissue of an organism. Moreover, the suturing mechanism portion has a plurality of staple lines for performing the suturing operation and a cutting mechanism, such as a knife, for cutting the tissue of an organism.

As a matter of course, use of the automatic suturing device in the surgical operation is advantageous in shortening the time required to complete the suturing and incision operations and in simplifying the operation.

In a case where the automatic suturing device is used when an operation of a weak tissue, such as the lung, the branch, the liver, the alimentary canal or the like is performed, the suturing operation using the staples has a risk that the tissue tears. In a case of an operation of, for example, the lung, there is a risk that air leakage takes place. Since the air leakage is a fatal problem for the patient, reliable prevention is required.

Accordingly, a method has been employed in which a suturing material is previously loaded into the automatic suturing device so as to be sutured to the excised portion of the tissue of an organism.

In this case, a contrivance is required to enable the suturing material to be loaded into the automatic suturing device so as to reliably be brought to the diseased part. For example, a structure has been suggested in which a knit cloth having flexibility is placed on a felt-type suturing material, followed by sewing the two side lines with tacking threads to form a cylindrical shape.

However, the suturing material formed by sewing the knit cloth having flexibility with the sewing thread so as to be loaded into the automatic suturing device can be contracted into the direction of insertion when the automatic suturing device is inserted into the organism to be brought to the diseased part, thus resulting in the suturing material being displaced to the base portion of the automatic suturing device or being turned around the automatic suturing device. That is, a problem of twisting takes place.

If the suturing material is displaced or turned, appropriate treatment cannot smoothly be performed. In particular, an operation of a type which is performed with an endoscope encounters a critical problem.

DISCLOSURE OF THE INVENTION

In view of the foregoing, an object of the present invention is to provide a medical suturing material which is capable of preventing displacement and turn when an automatic suturing device is inserted, for example, capable of reliably preventing air leakage when used in an operation of the lung.

To achieve the foregoing object, a medical suturing material according to the present invention is formed by sewing a sheet shape suturing material into a bag shape having a closed leading end by using a suturing thread so as to be loaded into an automatic suturing device having a staple line.

The suturing material according to the present invention has the main suturing material which may be a material, such as unwoven fabric such as felt, woven fabric or a knit cloth if it has somewhat flexibility and stretchability. A known material may be employed. In consideration of the state after the operation, it is preferable that bioabsorbable polymer, such as polyglycolic acid, or a portion of a tissue of an organism, for example, the organ protective film, such as the heart sac, be employed.

The above-mentioned suturing material may be formed into the bag shape by sewing one cloth material by the suturing thread or a plurality of, for example, two suturing materials, may be sewed into the bag shape. In the latter case, the two suturing materials may be the same material or may be different materials. Either of the two suturing materials may be a material except the suturing material, for example, a usual knit cloth.

Since the suturing material according to the present invention has the bag shape having the closed leading end by sewing, displacement taking place attributable to shrinkage in the insertion direction can be prevented when the automatic suturing device is inserted.

Since the suturing material formed into the bag shape from one or a plurality of suturing material by sewing has the structure in which the overall surface is made of only the suturing material, no problem arises even if it is unintentionally turned (twisted).

BEST MODE FOR CARRYING OUT THE INVENTION

Preferred embodiments of the present invention will now be described in detail with reference to the drawings.

Embodiment 1

Figure 1:
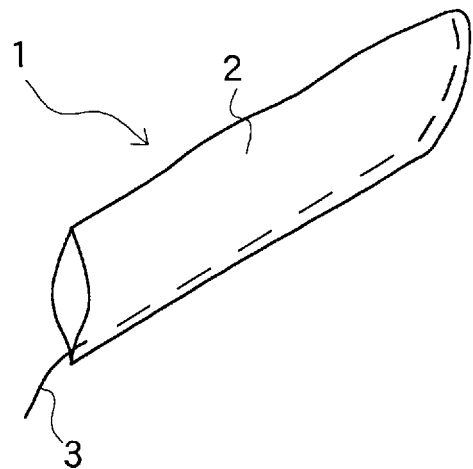
FIG. 1 is a schematic perspective view showing an example of a suturing material according to the present invention.

A medical suturing material 1 according to this embodiment, as shown in FIG. 1, is in the form of a bag shape having a closed leading end by sewing one main suturing material 2 made of felt (for example, NEOVEIL which is trade name of Gunze Kabushiki Kaisha) composed of, for example absorbable polyglycolic acid by using a suturing thread. As described above, the structure is very simple.

The main suturing material 2 may be a known suturing material as well as the bioabsorbable polymer, such as the absorbable polyglycolic acid. For example, a portion of a tissue of an organism, such as an organ protective film exemplified by the heart sac, may be employed.

The main suturing material 2 is formed into an elongated shape having a length which is substantially the same as that of a loading portion of an automatic suturing device to be described later. The main suturing material 2 is folded into two, and then sewed along one side portion in the widthwise direction by a suturing thread 3 which is a thread for suturing.

It is preferable that the suturing threads 3 be so-called monofilaments in view of easy drawing, while the material of the same may be determined arbitrarily. For example, an bioabsorbable polymer thread or a polyamide thread (trade name: Nylon Thread) having excellent sliding characteristic may preferably be employed.

The medical suturing material having the above-mentioned structure is loaded into the automatic suturing device. The structure of the automatic suturing device and the method to use the medical suturing material according to this embodiment will now be described.

Figure 2:
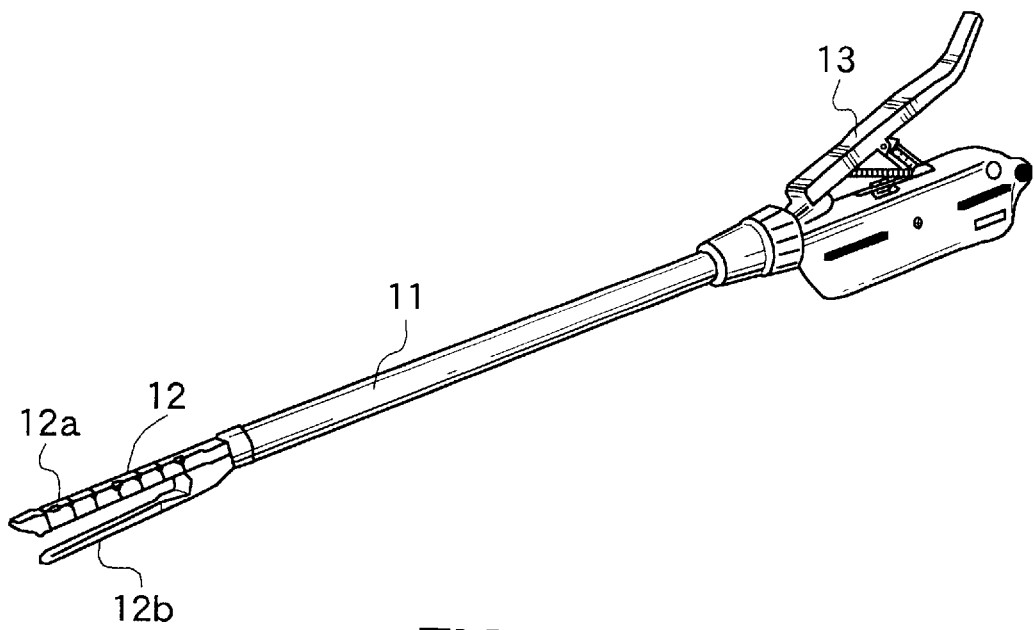
FIG. 2 is a schematic perspective view showing an example of an automatic suturing device in which the suturing material is used.

As shown in FIG. 2, the automatic suturing device has, at the leading end of a shaft 11 thereof, a suturing portion 12 which can be opened/closed. The automatic suturing device has, in the base portion thereof, an operation portion 13 which is arranged to be held and with which operation of the automatic suturing device is performed.

Figure 3:
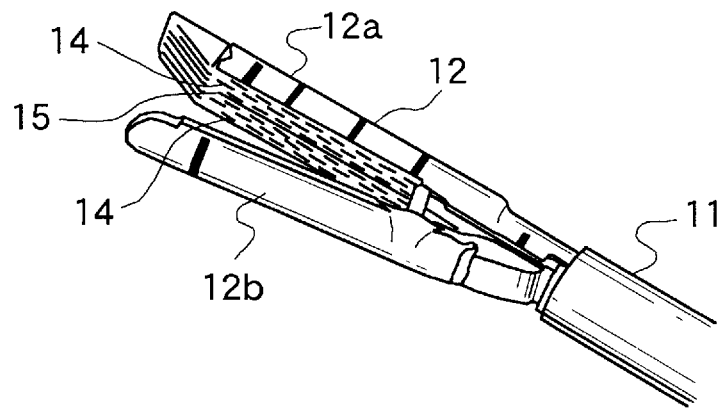
FIG. 3 is a schematic plan view showing an essential portion of a suturing mechanism portion of the automatic suturing device.

As shown in FIG. 3, the suturing portion 12 has a suturing mechanism portion 12a on which a cartridge accommodating staples and a knife blade are mounted; and a jaw portion 12b for holding a tissue of an organism. A plurality of (3 lines×3 lines=6 lines) of staple lines 14 and knife scanning line 15 face the holding surface of the suturing mechanism portion 12a.

The automatic suturing device is introduced into the organism through an attachment called a "surge boat". That is, the surge boat is attached to a perforation formed in the organism, and then the shaft 11 of the automatic suturing device is inserted into the organism through the surge boat. As a result, the perforation formed in the organism can be sealed up.

Figure 4:
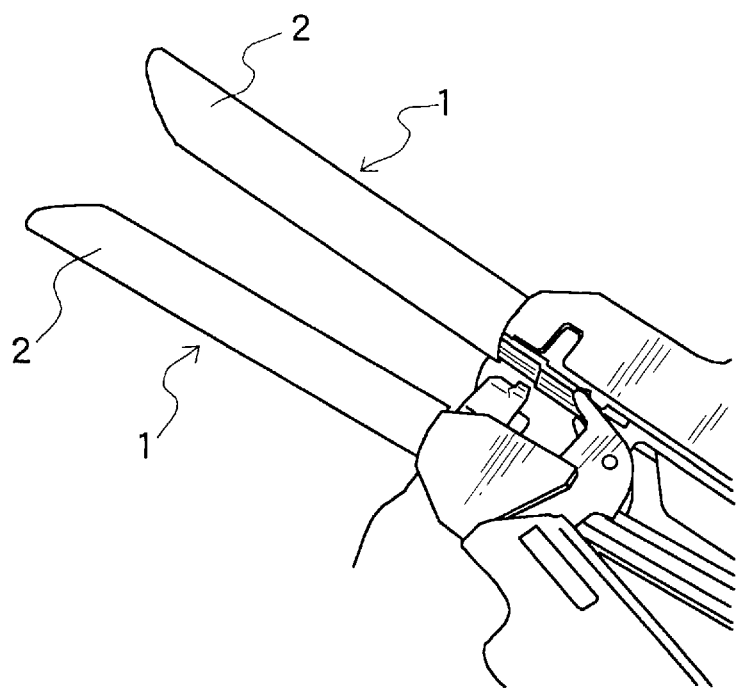
FIG. 4 is a schematic perspective view showing a state where the suturing material has been loaded into the automatic suturing device.

The medical suturing material 1 is loaded into the suturing portion 12 of the automatic suturing device when used. FIG. 4 shows a state where the suturing material 1 has been loaded into the suture portion 12 of the automatic suturing device such that the suturing material 1 is attached to the suturing mechanism portion 12a and jaw portion 12b.

The suturing material 1 can smoothly be loaded into the suture portion 12 by covering the suture portion 12 with the bag shape suturing material 1.

In the above-mentioned state, the automatic suturing device is inserted into the organism through the surge boat as described above to be brought to the diseased part. Since the suturing material 1, to be loaded into the automatic suturing device, has a shape arranged such that the closed portion of the bag structure is pushed in, displacement and twisting can be prevented.

Figure 5:
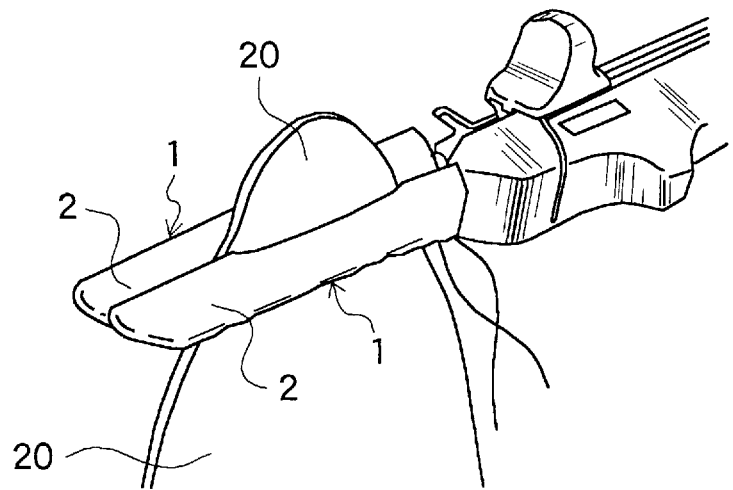
FIG. 5 is a schematic perspective view showing a state of a suturing operation by using the automatic suturing device.

After the suture portion 12 has been introduced into the diseased part, the excised portion of the tissue of an organism 20 is held by the suturing mechanism portion 12a and jaw portion 12b, as shown in FIG. 5. As a result, the excised portion is covered with the main suturing material 2.

Then, an operation lever 13a provided for the operation portion 13 of the automatic suturing device is operated so that staples are driven through the operation portion 13.

As a result, the staples are driven along the excised portion of the tissue of the organism 20 so that the suturing treatment is performed. Simultaneously, the main suturing material 2 of the suturing material 1 loaded into the suture portion 12 is pressed against the excised portion of the tissue of the organism 20 so as to be sutured by the staples.

The main suturing material 2 serves as a reinforcing member when the suturing operation is performed. By suturing the cut portion of the tissue of the organism 20 through the main suturing material 2, tearing of the tissue can be prevented. Thus, for example, an excision operation of a great sacculus alveolaris can be performed without air leakage.

Then, the knife provided for the suturing mechanism portion 12a is scanned along the scanning lines 15 to cut the tissue of the organism 20 and the main suturing material 2.

Figure 6:
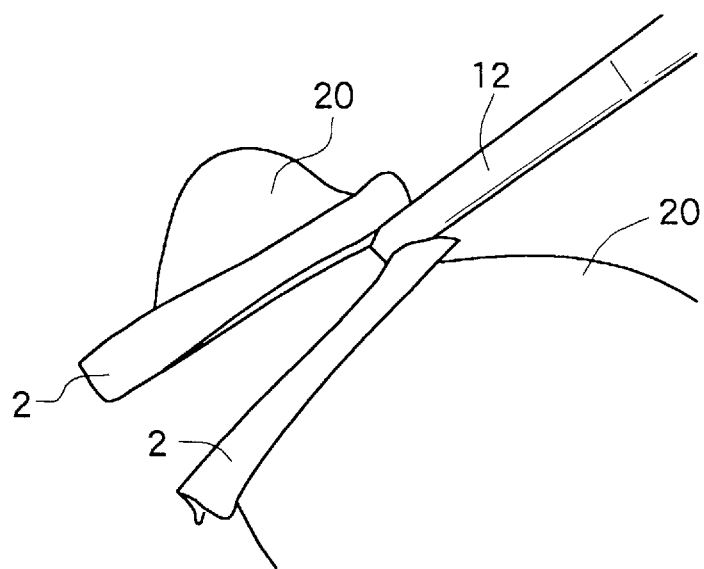
FIG. 6 is a schematic perspective view showing a state where the suturing treatment has been completed.

Thus, the suturing treatment is completed. By using the suturing material 1 according to this embodiment, the suturing operation can smoothly be performed. Moreover, the sutured portion can reliably be reinforced and air leakage from the same can be prevented. FIG. 6 shows a state of completion of the suturing operation, in which the main suturing material 2 is joined to the sutured portion of the tissue of the organism 20 by the suturing operation. The state of suturing can significantly be stabilized.

Embodiment 2

Figure 7:
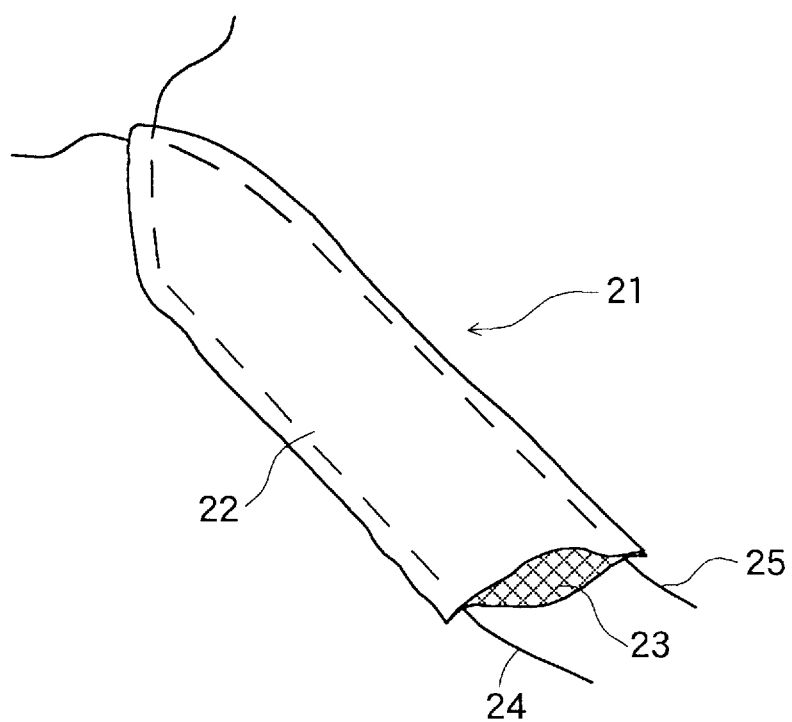
FIG. 7 is a schematic perspective view showing another example of the suturing material according to the present invention.

A suturing material 21 according to this embodiment is, as shown in FIG. 7, formed by sewing two suturing materials 22 and 23 into a bag shape having a closed leading end.

Each of the suturing materials 22 and 23 is formed into a shape having a width which is reduced in a direction toward the leading end thereof. The two side ends are sewed by suturing threads 24 and 25. The suturing threads 24 and 25 are made to intersect at the leading ends of the suturing materials 22 and 23 correspondent to the shapes of the suturing materials 22 and 23 so that sewing of the bag structure is made reliable.

The suturing materials 22 and 23 may be made of the same material or different materials. Specifically, the first suturing material 22 is made of felt of absorbable polyglycolic acid (for example, NEOVEIL which is trade name of Gunze Kabushiki Kaisha), while the second suturing material 23 is made of another material.

By using different materials, the cost can be reduced and therefore an advantage can be realized in the manufacturing process.

Also the suturing material according to this embodiment is, similarly to the suturing material according to Embodiment 1, loaded into the automatic suturing device when used. The method of use of the same is similar to that according to Embodiment 1.

Although the invention has been described in its preferred form with a certain degree of particularity, it is understood that the present disclosure of the preferred form can be changed in the details of construction and in the combination and arrangement of parts.

INDUSTRIAL APPLICABILITY

The suturing material according to the present invention is able to prevent displacement taking place attributable to shrinkage when the automatic suturing device is inserted. Even if twisting takes place, the suturing material can always be in contact with the diseased part.

Therefore, use of the suturing material according to the present invention enables the sutured portion to be reinforced reliably. As a result, tearing of the tissue and air leakage can be prevented.

We claim:

1. In combination with an automatic suturing device used for suturing and cutting tissue, the automatic suturing device having a suturing mechanism portion, and a jaw portion:

a medical suturing material comprising at least one sheet of a flexible main suturing material sewn into a bag shape having a closed leading end by at least one suturing thread, the suturing thread being drawable wherein said medical suturing material is loaded into said suturing mechanism portion.

2. The combination as in to claim 1, wherein said at least one sheet of a flexible main suturing material is selected from a group consisting of unwoven fabric, woven fabric and a knit cloth.

3. The combination as in to claim 2, wherein said at least one sheet of a flexible main suturing material is made of synthetic polymer.

4. The combination as in to claim 3, wherein said synthetic polymer is bioabsorbable polymer.

5. The combination as in to claim 4, wherein said bioabsorbable polymer is polyglycolic acid.

6. The combination as in to claim 1, wherein said at least one sheet of a flexible main suturing material comprises tissue of an organism.

7. The combination as in to claim 6, wherein said tissue of an organism is an organ protective film.

8. The combination as in to claim 7, wherein said tissue of an organism is a heart sac.

9. The combination as in claim 1, comprising two sheets of flexible main suturing material.

10. The combination as in claim 9, wherein said two sheets of flexible main suturing material are of different material.

* * * * *